Figure 1:
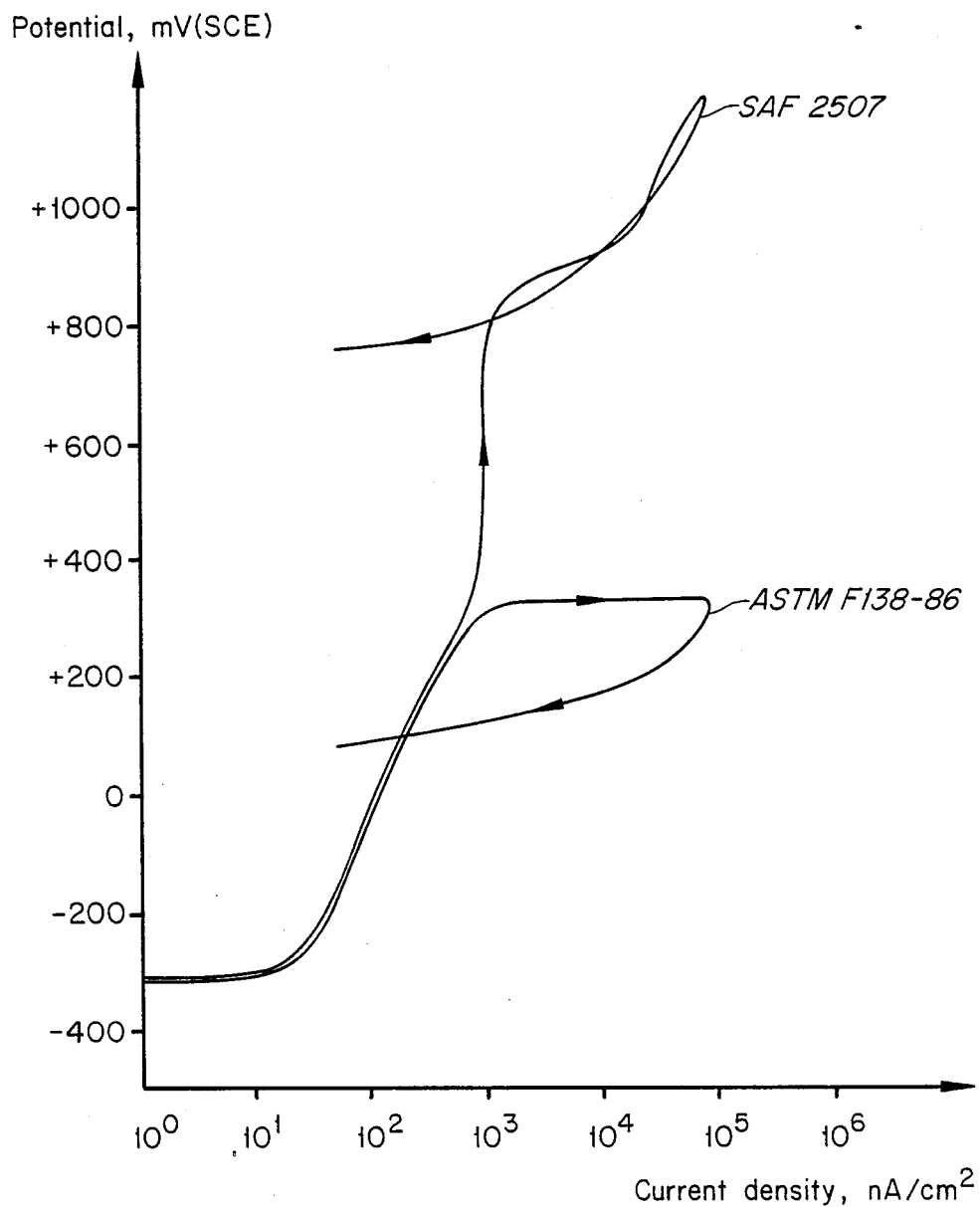

United States Patent [19]

Hagenfeldt et al.

[11] Patent Number: 4,964,925

[45] Date of Patent: * Oct. 23, 1990

[54] MEDICAL IMPLANT MADE OF A STAINLESS STEEL ALLOY

[75] Inventors: Carl P. U. Hagenfeldt, Estoril, Portugal; Annika M. Roos, Sandviken, Sweden

[73] Assignee: Sandvik AB, Sweden

[*] Notice: The portion of the term of this patent subsequent to Aug. 23, 2005 has been disclaimed.

[21] Appl. No.: 332,178

[22] Filed: Apr. 3, 1989

[30] Foreign Application Priority Data

Apr. 21, 1988 [SE] Sweden .............................. 88014741

[51] Int. Cl.⁵ .......................................... C22C 38/44
[52] U.S. Cl. .................................. 148/325; 148/327; 623/16; 606/76
[58] Field of Search ......................... 623/16; 128/92 R; 433/201.1; 148/325, 327; 420/57, 58, 59, 52, 65, 67

[56] References Cited

U.S. PATENT DOCUMENTS 4,765,953  8/1988  Hagenfeldt et al. ............... 148/327
4,775,426  10/1988  Murley et al. ...................... 148/327

FOREIGN PATENT DOCUMENTS 2457089  6/1975  Fed. Rep. of Germany ...... 148/325
2160892  1/1986  United Kingdom ............... 148/325

Primary Examiner—Deborah Yee

[57] ABSTRACT

The invention advises use of a stainless steel alloy of ferritic-austenitic structure as implant in physiological environments, said alloy containing in weight percent max 0.05% C, 23–27% Cr, 5.5–9.0% Ni, 0.25–0.40% N, max 0.8% Si, max 1.2% Mn, 3.5–4.9% Mo, max 0.5% Cu, max 0.5% W, max 0.010% S, up to 0.5% V, up to 0.18% Ce and the balance Fe and normal impurities, whereby the ferrite content amounts to 30–55%.

2 Claims, 2 Drawing Sheets

MEDICAL IMPLANT MADE OF A STAINLESS STEEL ALLOY

The present invention relates to the use of a stainless steel alloy, more specifically a ferritic-austenitic stainless steel alloy for the manufacture of medical implants. An implant is a piece that is permanently or temporarily operated into a body web. The material is characterized by improved corrosion resistance in aggressive chloride environments, good mechanical and physical properties, good fatigue properties and good biocompatibility.

The two types of materials that have primarily been used as materials for medical implants are titan alloys and austenitic stainless steel materials. Titan alloys are unfavorable because they are very expensive for making prostheses and similar items. The austenitic steel material with designation ASTM F138-86 that has been used is a Cr-Ni-Mo-steel alloy containing 17–19% Cr, 13–15.5% Ni, 2–3% MO, max 0.03% C, max 0.10% N, the remainder being Fe and impurities in normal amounts. This type of material is however problematic for use in implants due to its corrosion, erosion and insufficiencies due to fatigue.

In accordance with the present invention a ferritic-austenitic steel alloy containing 30–55% ferrite with properly optimized constituents has been found to be well suitable for use in environments where presence of chloride ions, such as in human body web, give rise to high corrosion. The applicable steel alloy contains in weight percent from traces up to 0.05% C, 23–27% Cr, 5.5–9.0% Ni, 0.25–0.40% N, max 0.8% Si, max 1.2% Mn, 3.5–4.9% Mo, max 0.5% Cu, max 0.5% W, max 0.010% S, max 0.5% V, max 0.18% Ce and Fe and normal impurities, and in which the contents of the alloying elements are so adjusted that the following conditions are fulfilled:

$$\frac{\% \text{Mn}}{\% \text{N}} < 3$$

and % Cr+3.3% Mo+16% N−1.6% Mn−122% S>39.1 and the ferrite content is between 30% and 55%. The alloy defined above which has good structure stability and good workability will in the following be given the designation SAF 2507.

The corrosion properties are specifically important for a material which shall be well suited for use in physiological environments, such as artificial body liquid containing about 0.9% NaCl-solution and a temperature about 37° C. In order to investigate the corrosion resistance this material SAF 2507 has been subjected to tests together with an austenitic material having designation ASTM F138-86. Both materials have been subjected to following electrochemical testing methods:
 (a) cyclic potentiodynamic polarization test
 (b) ASTM F746-81
 (c) pH-depassivation
 (d) CPT-critical temperature for pitting corrosion.

FIG. 1 illustrates the results of test method (a) above where the potential (mV in relation to SCE*) is shown as a function of the current density (nA/cm$^2$).
*SCE - standard calomel electrode By means of this method the resistance against initiation and propagation of pitting and crevice corrosion is determined. The polarization curves obtained for SAF 2507 and ASTM F138-86 and their different behaviour indicate clear differences in regard of the corrosion properties. SAF 2507 thus appears to have a break-through potential of about +800 mV and corrosion first propagates at potentials on same approximate level. Considerably lower values were obtained for ASTM F138-86; a break-through potential of about +300 mV and a propagation potential of about +100 mV. Test method (b) which is usually referred to under designation ASTM F746-81 is the only standardized test method for investigation of resistance against pitting and crevice corrosion for new metallic implant materials. This method determines break-through potential and critical potential. Table 1 below shows the results obtained.

TABLE 1

| Steel alloy | Critical potential (mV) |
| --- | --- |
| SAF 2507 | >+800 |
| ASTM F138-86 | +250 |

As appears herefrom SAF 2507 has a considerably higher break-through potential than ASTM F138-86 which indicates improved corrosion resistance.

Test method (c) above uses the potentiometric polarization measurements to determine the corrosion resistance in acid environments. This is also a measure of the resistance against pitting and crevice corrosion. Table 2 below shows the measurement results obtained.

TABLE 2

| Steel alloy | pH |
| --- | --- |
| SAF 2507 | 0.96 |
| ASTM F138-86 | 1.35 |

The material SAF 2507 thus shows a clearly lower measure of depassivation-pH which indicates improved corrosion resistance.

Figure 2:
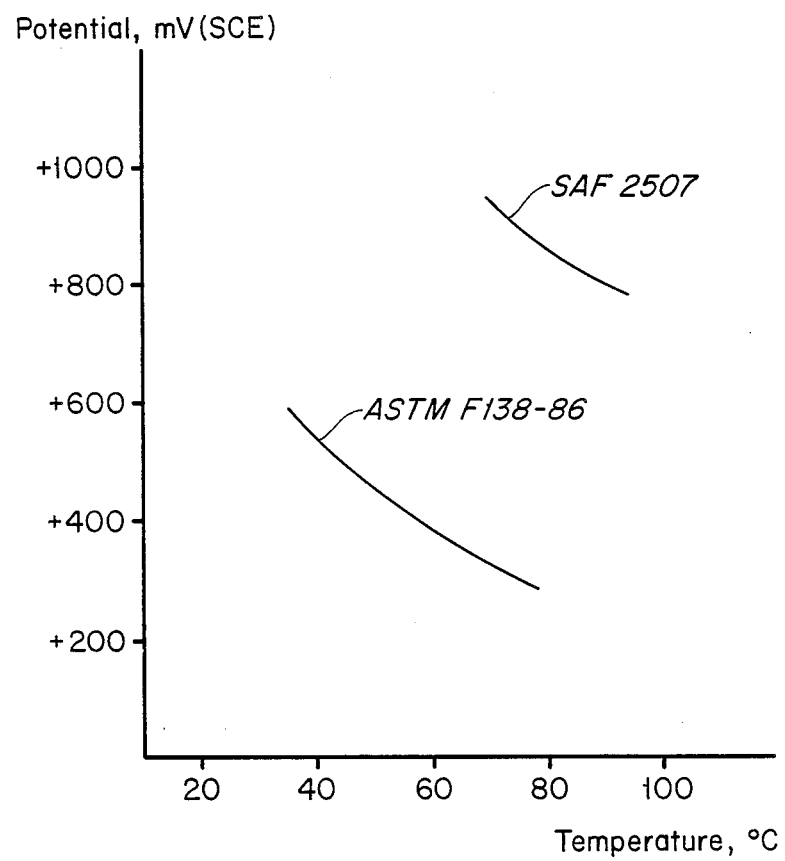

Test method (d) is based on measurement of the temperatures for which current break-through occurs at different applied potentials. The temperatures and level of potential indicate the resistance against pitting corrosion attacks. FIG. 2 shows the results obtained from these measurements. As appears from the obtained CPT-curves values have been obtained for SAF 2507 that are clearly superior in comparison with those obtained for ASTM F138-86.

In order to ascertain the biocompatibility properties of the material three different part tests have been made in cell cultures that are grown from web taken from an oral cavity. In parallel with SAF 2507 both stainless steel according to ASTM 138-86 and titan have been included.

Part test No. 1 included a study of the cell colony formation ability and their growth rate during 8 days of exposure of the test materials. The values are compared with the values obtained from cells without exposure of material. Table 3 below shows the measured values that were obtained.

TABLE 3

| Material | CFE[a] | CGR[b] |
| --- | --- | --- |
| SAF 2507 | 100% | 0.8 |
| ASTM F138-86 | 100% | 0.8 |
| Titan | 100% | 0.8 |
| Control | 100% | 0.8 |

[a]Colony formation ability
[b]Colony growth rate

The measured values were thus equal for all materials.

Part test No. 2 included investigation of the adaptation of cells to the surface of the test material and registration of an eventual cell-lysis zone. This test was on-going for 10 days. No cell-lysis zone could be found for any of the materials and the cell adaptation was equal for all materials.

Part test No. 3 included an investigation of the emission of eventual metal ions and/or ion aggregates from the materials. The test items were kept for 3 weeks in a web growth medium after which they were subjected to investigations in accordance with part test No. 1. Table 4 below shows the measured values that were obtained.

TABLE 4

| Material | CFE | CGR |
| --- | --- | --- |
| SAF 2507 | 100% | 0.8 |
| ASTM F138-86 | 95% | 0.8 |
| Titan | 90% | 0.7 |
| Control | 100% | 0.8 |

As appears from the measured values SAF 2507 appears to have the best colony formation ability whilst simultaneously having good growth rate in level with the compared materials.

The mechanical properties have been investigated by measuring yield strength, tensile strength, elongation and hardness for materials in quench-annealed condition at 20° C. (68° F.) which corresponds with those conditions that are required for ASTM-specifications. Table 5 below shows the measured values obtained.

TABLE 5

|  | Yield 0.2% N/mm² min | strength PSI min | Tensile N/mm² min | strength PSI min | Elong. A5 % min | Hardness Vickers ca |
| --- | --- | --- | --- | --- | --- | --- |
| SAF 2507 | 550 | 79800 | 800 | 116000 | 15 | 260–290 |
| ASTM F138-86 | 190 | 27600 | 490 | 71100 | 45 | 150 |

Thus, the measured values for SAF 2507 are clearly better than those for the comparison material ASTM F138-86. The above given measured values for hardness also indicate that SAF 2507 has better erosion properties since erosion resistance is closely associated with the hardness. The hardness of the duplex structure thus contributes to better erosion resistance for SAF 2507 than compared with the austenitic material ASTM F138-86.

We claim:

1. An implant having good corrosion resistance in physiological environments including a body-liquid containing about 0.9% NaCl solutions at 37° C. comprising, a stainless steel alloy with ferritic-austenitic structure containing in weight percent, max 0.05% C, 23–27% Cr, 5.5–9.0% Ni, 0.25–0.40% N, max 0.8% Si, max 1.2% Mn, 3.5–4.9% Mo, max 0.5% Cu, max 0.5% W, max 0.010% S, up to 0.5% V, up to 0.18% Ce, the balance Fe and normal impurities, in which the ferrite content is 30–55%.

2. The implant of claim 1, wherein the contents of the alloying elements are adjusted so that the following conditions are fulfilled:

$$\frac{\% \text{Mn}}{\% \text{N}} < 3$$

and % Cr+3.3% Mo+16% N−1.6% Mn−122% S>39.1.

* * * * *